United States Patent

Ryan, Jr. et al.

[11] Patent Number: 5,935,809
[45] Date of Patent: Aug. 10, 1999

[54] METHOD OF INDUCING PLANT DEFENSE MECHANISMS

[75] Inventors: Clarence A. Ryan, Jr., Pullman, Wash.; Edward E. Farmer, Preverenges, Switzerland

[73] Assignee: Washington State University Research Foundation, Pullman, Wash.

[21] Appl. No.: 08/280,172

[22] Filed: Jul. 25, 1994

Related U.S. Application Data

[63] Continuation of application No. 07/979,540, Nov. 23, 1992, abandoned, which is a continuation of application No. PCT/US91/03685, May 24, 1991, which is a continuation-in-part of application No. 07/528,956, May 25, 1990, abandoned.

[51] Int. Cl.⁶ ............................ C12N 21/00; C12N 15/00
[52] U.S. Cl. ........................ 435/69.1; 536/24.1; 800/278
[58] Field of Search ........................ 800/205; 435/172.3, 435/69.1, 170.1; 47/58.03, 58.05; 536/24.1, 24.2; 549/484

[56] References Cited

FOREIGN PATENT DOCUMENTS

| | | |
|---|---|---|
| 0272144 | 6/1988 | European Pat. Off. . |
| 0332104 A3 | 9/1989 | European Pat. Off. . |
| 0375091 A1 | 6/1990 | European Pat. Off. . |
| 241821 | 1/1987 | Germany . |
| WO89/12230 | 12/1989 | WIPO . |

OTHER PUBLICATIONS

Johnson, R. et al., "Expression of Proteinase Inhibitors I and II in Transgenic Tobacco Plants: Effects on Natural Defense Against *Manduca sexta* Larvae," *Proc. Natl. Acad. Sci. USA* 86:9871–9875, 1989.

Ecker, J.R et al., "Plant Defense Genes Are Regulated by Ethylene," *Proc. Natl. Acad. Sci. USA* 84:5202–5206, 1987.

Sanchez–Serrano, J.J. et al., "Wound–Induced Expression of a Potato Proteinase Inhibitor II Gene in Transgenic Tobacco Plants," *EMBO J.* 6:303–306, 1987.

Bohlmann, H. et al., "Leaf–Specific Thionins of Barley–A Novel Class of Cell Wall Proteins Toxic to Plant–Pathogenic Fungi and Possibly Involved in the Defence Mechanism of Plants," *EMBO J.* 7(6):1559–1565, 1988.

Cramer, C.L. et al., "Co–ordinated Synthesis of Phytoalexin Biosynthetic Enzymes in Biologically–Stressed Cells of Bean," *EMBO J.* 4(2):285–289, 1985.

Saniewski, M. et al., "The Effect of Methyl Jasmonate on Ethylene Production and Ethylene–Forming Enzyme Activity in Tomatoes," *J. Plant Physiol.* 129:175–180, 1987.

Parthier, B., "Jasmonates: Hormonal Regulators or Stress Factors in Leaf Senescence?" *J. Plant Growth Regul.* 9:57–63, 1990.

Anderson, J.M. et al., "Jasmonic Acid–Dependent Increase in the Level of Vegetative Storage Proteins in Soybean," *Plant Science* 62:45–52, 1989.

Herrmann, G. et al., "Species and Tissue Specificity of Jasmonate–Induced Abundant Proteins," *J. Plant Physiol.* 134:703–709, 1989.

Meyer, A. et al., "Occurence of the Plant Growth Regulator Jasmonic Acid in Plants," *Journal of Plant Growth Regulation*, 3:1–8, 1984.

(List continued on next page.)

*Primary Examiner*—Gary Benzion
*Attorney, Agent, or Firm*—Christenson, O'Connor, Johnson & Kindness PLLC

[57] ABSTRACT

The expression of plant defense proteins is induced in plant tissue by contacting plants to be treated with a defense protein inducing agent. The inducing agent, which may be jasmonic acid, lower alkyl esters of jasmonic acid or jasmonic acid-like derivative compounds, induces the expression of genes in the plants resulting in the production of defense proteins, such as proteinase inhibitors, thionins, chitinases and β-glucanases. Plants may be contacted with the inducing agent by direct application to plant tissue or by airborne transmission of the inducing agent.

10 Claims, 7 Drawing Sheets

OTHER PUBLICATIONS

Hilder, V.A. et al., "A Novel Mechanism of Insect Resistance Engineered into Tobacco," *Nature* 330:160–163, 1967.

Darvill, A.G. et al., "Phytoalexins and Their Elicitors—A Defense Against Microbial Infection in Plants," *Ann. Rev. Plant Physiol.* 35:243–275, 1984.

Lawton, M.A. et al., "Transcriptional Activation of Plant Defense Genes by Fungal Elicitor, Wounding, and Infection," *Mol. Cell Biol.* 7:335–341, 1987.

Ryan, C.A., "Oligosaccharide Signalling in Plants," *Ann. Rev. Cell Biol.* 3:295–317, 1987.

Green, T.R. et al., "Wound–Induced Proteinase Inhibitor in Plant Leaves: A Possible Defense Mechanism Against Insects," *Science* 175:776–777, 1972.

Kuc J. et al., "Fungal Regulation of Disease Resistance Mechanisms in Plants," *Mycologia* 76:767–784, 1984.

Kopp, M. et al., "Host–Pathogen Interactions XXXII. A Fungal Glucan Preparation Protects Nicotianae Against Infection by Viruses," *Plant Physiol.* 90:208–216, 1989.

Hammond–Kosack, K.E. et al., "Systemic Accumulation of Novel Proteins in the Apoplast of the Leaves of Potato Plants Following Root Invasion by the Cyst–Nematode *Globodera Rostochiensis,*" *Physiol. Mol. Plant Path.* 35:495–506, 1989.

Baldwin, I.T. et al., "Rapid Changes in Tree Leaf Chemistry Induced by Damage: Evidence for Communication Between Plants," *Science* 221:277–278, 1983.

Rhoades, D.F., "Responses of Alder and Willow to Attack by Tent Caterpillars and Webworms: Evidence for Pheromonal Sensitivity of Willows," In Plant Resistance to Insects, (P. Hedin, Ed.), American Chemical Society, Washington, D.C., 1983.

Zeringue, H.J., Jr., "Effects of $C_6$–$C_{10}$ Alkenals and Alkanals on Eliciting a Defence Response in the Developing Cotton Boll, " *Phytochemistry* 31(7):2305–2308, 1992.

Vick, B.A. et al., "Biosynthesis of Jasmonic Acid by Several Plant Species," *Plant Physiol.* 75:458–461, 1984.

Anderson, J.M., "Membrane–Derived Fatty Acids as Precursors to Second Messengers," In Second Messengers in Plant Growth and Development, Alan R. Liss, Inc., pp. 181–212, 1989.

Dathe, W. et al., "Endogenous Plant Hormones of the Broad Bean, *Vicia faba* L. (—)–Jasmonic Acid, a Plant Growth Inhibitor in Pericarp," *Planta* 153:530–535, 1981.

Yamane, H. et al., "Identification of Jasmonic Acid in Three Species of Higher Plants and Its Biological Activities," *Plant Cell Physiol.* 22:689–697, 1981.

Ueda, J. et al., "Isolation and Identification of a Senescence–Promoting Substance from Wormwood (*Artemisia absinthium* L.)," *Plant Physiol.* 66:246–249, 1980.

Curtis, R.W., "Abscission–Inducing Properties of Methyl Jasmonate, ABA, and ABA–Methyl Ester and Their Interactions With Ethephon, $AgNo_3$, and Malformin," *Plant Growth Regul.* 3:157–168, 1984.

Mueller–Uri, J. et al., "Jasmonate–Induced Alteration of Gene Expression in Barley Leaf Segments Analyzed by in–vivo and in–vitro Protein Synthesis," *Planta* 176:241–247, 1988.

Staswick, P.E., "Novel Regulation of Vegetative Storage Protein Genes," *The Plant Cell* 2:1–6, 1990.

Lee, J.S. et al., "Molecular Characterization and Phylogenetic Studies of a Wound–Inducible Proteinase Inhibitor I Gene in Lycopersicon Species," *Proc. Natl. Acad. Sci. USA* 83:7277–7281, 1986.

Cleveland, T.E. et al., "Molecular Characterization of a Wound–Inducible Inhibitor I Gene From Potato and the Processing of its mRNA and Protein," *Plant Mol. Biol.* 8:199–207, 1987.

Graham, J.S. et al., "Wound–Induced Proteinase Inhibitors from Tomato Leaves: I. The cDNA–Deduced Primary Structure of Pre–Inhibitor I and its Post–Translational Processing," *J. Biol. Chem.* 260:6555–6560, 1985.

Graham, J.S. et al., "Wound–Induced Proteinase Inhibitors from Tomato Leaves: II. The cDNA–Deduced Primary Structure of Pre–Inhibitor II," *J. Biol. Chem.* 260:6561–6564, 1985.

Thornburg R.W. et al., "Wound–Inducible Expression of a Potato Inhibitor II–Chloramphenicol Acetyltransferase Gene Fusion in Transgenic Tobacco Plants," *Proc. Natl. Acad. Sci. USA* 84:744–748, 1987.

Chem Abstract, 112:33479x, Saniewski, M., "Relationship Between Stimulatory Effect of Methyl Jasmonate on Gum Formation and Ethylene Production in Tulip Stem," *Bull. Pol. Acad. Sci.: Biol. Sci.*, 37(1–3), 41–8, 1989.

Pena–Cortes, H. et al., "Abscisic acid is involved in the wound–induced expression of the proteinase inhibitor II gene in potato and tomato," *Proc. Natl. Acad. Sci. USA*, 86:9851–9855 (1989).

Farmer, E.E. et al., "In vitro phosphorylation of plant plasma membrane proteins in response to the proteinase inhibitor inducing factor," *Proc. Natl. Acad. Sci. USA*, 86:1539–1542 (1989).

Keil, M. et al., "Both wound–inducible and tuber–specific expression are mediated by the promoter of a single member of the potato proteinase inhibitor II gene family," *EMBO J.*, 8:1323–1330 (1989).

Johnson et al. (1989) PNAS, vol. 86: pp. 9871–9875.

Ecker et al. (1987) PNAS, vol. 84: pp. 5202–5206.

Sanchez–Serrano et al. (1987) EMBO Journal, vol. 6: pp. 303–306.

Bohlmann et al. (1988) EMBO Journal, vol. 7: pp. 1559–1565.

Cramer et al. (1985) EMBO Journal, vol. 4: pp. 285–289.

Saniewski et al. (1987) J. Plant Physiol., vol. 129(1–2): pp. 175–180.

```
GATCTTTGAAATTAGACAAGTATTATCGGACATCTACTTTTAGTATAGTAAACAAAGTAA    60
AGATCGATAAAGAGAGTAATAAAGAAGAAGCAAGCGTAAGTACCTTGCCAAATAATTAA   120
CTAACAAGCACATCTTTTTTTTTATCAAATATTAATAAAATAATTTATATTAATATGA    180
AGAAAAAAGGTTTTAGTTTGCTATCTTTTTGATCACTCGTTTGCTATAAATAGGTGGA    240
GGAGGACAGAGACACTCTTCACCCCAAATTAAAAGAAAAAGAGGCAGTACTAATTAATTAT 300

CCATC ATG GAT GTT CAC AAG GAA GTT AAT TTC GTT GCT TAC CTA CTA  347
      Met Asp Val His Lys Glu Val Asn Phe Val Ala Tyr Leu Leu

ATT GTT CTT G  GTAAGATTTTCCTTTACTCCTTTTTTTTTTAAAAAA AAAATTCTTG 407
Ile Val Leu G--

TTTATACATATATATATATATACACAAGTAGTTTTATATTTTTCCTTTATATTATATTTG 467

TTTGTAG GA TTA TTG GTA CTT GTA AGC GCG ATG GAT GTT GAT GCG AAG 515
     -ly Leu Leu Val Leu Val Ser Ala Met Asp Val Asp Ala Lys

GCT TGC ATT AGA GAA TGT GGT AAT CTT GGG TTT GGG ATA TGC CCA CGT 563
Ala Cys Ile Arg Glu Cys Gly Asn Leu Gly Phe Gly Ile Cys Pro Arg

TCA GAA GGA AGT CCG GAA AAT CCG GAA AAC TGT ACC AAC TGT TGT GCA GGT 611
Ser Glu Gly Ser Pro Glu Asn Pro Glu Asn Cys Thr Asn Cys Cys Ala Gly
```

Fig. 6A

```
TAT AAA GGT TGC AAT TAT TAT AGT GCA AAT GGG GCT TTC ATT TGT GAA  659
Tyr Lys Gly Cys Asn Tyr Tyr Ser Ala Asn Gly Ala Phe Ile Cys Glu

GGA CAA TCT GAC CCA AAA AAA CCA AAA GCA TGC CCC CTA AAT TGC GAT  707
Gly Gln Ser Asp Pro Lys Lys Pro Lys Ala Cys Pro Leu Asn Cys Asp

CCA CAT ATT GCC TAC TCA AAG TGT CCC CGT TCA GAA GGA AAA TCG CTA  755
Pro His Ile Ala Tyr Ser Lys Cys Pro Arg Ser Glu Gly Lys Ser Leu

ATT TAT CCC ACC GGA TGT ACC ACA TGC TGC ACA GGG TAC AAG GGT TGC  803
Ile Tyr Pro Thr Gly Cys Thr Thr Cys Cys Thr Gly Tyr Lys Gly Cys

TAC TAT TTC GGT AAA AAT GGC AAG TTT GTA TGT GAA GGA GAG AGT GAT  851
Tyr Tyr Phe Gly Lys Asn Gly Lys Phe Val Cys Glu Gly Glu Ser Asp

GAG CCC AAG GCA AAT ATG TAC CCT GCA ATG TGACCCTAGACTTGTCCATCTTC  904
Glu Pro Lys Ala Asn Met Tyr Pro Ala Met ***

TGGATTGCCAAGTTAATTAATGTATGAAATAAAGGATGCACACATAGTGACATGCTAA    964
TCACTATAATGTGGGCATCAAAGTTGTGTG TTATGTGTAATAACTAATTATCTGAATAAG  1024
AGAAAGAGAGATCATCCATATTCTTATCCTAAATGAATGACAGTGTCTTTATAATTCTT   1084
TGATGAACAGATGCATTTTATTAACCAATTCCATATACATATAAATATTAATCATATATA  1144
ATTAATATCAATTGGTTAGCAAAACCCAAATCTAGTCTAGGTGTGTTTTGCTAATTATGG  1204
GGGATAGAGCAAAAAGAAAACTAACGTCTCAAGAATC  1241
```

Fig. 6B

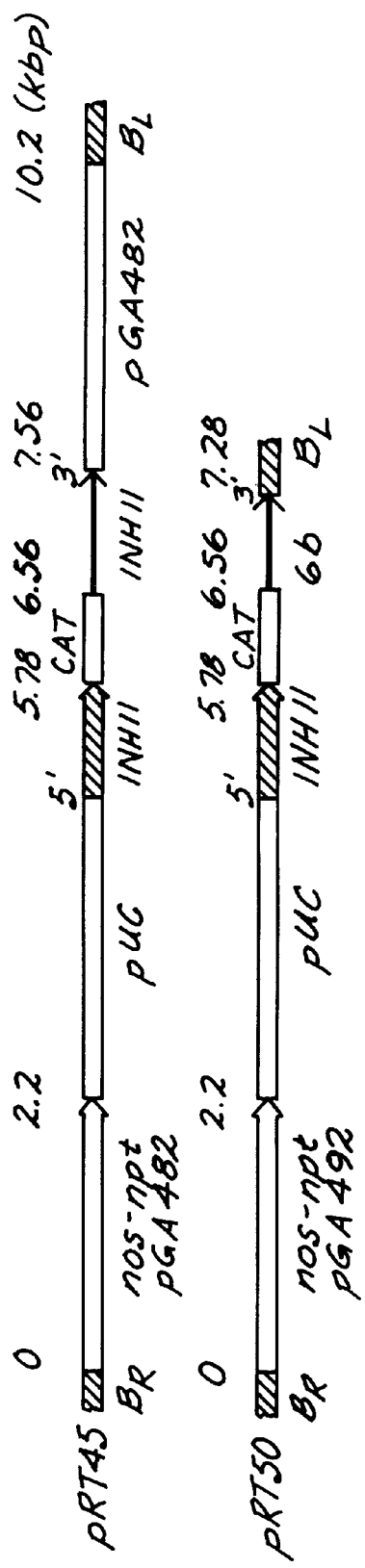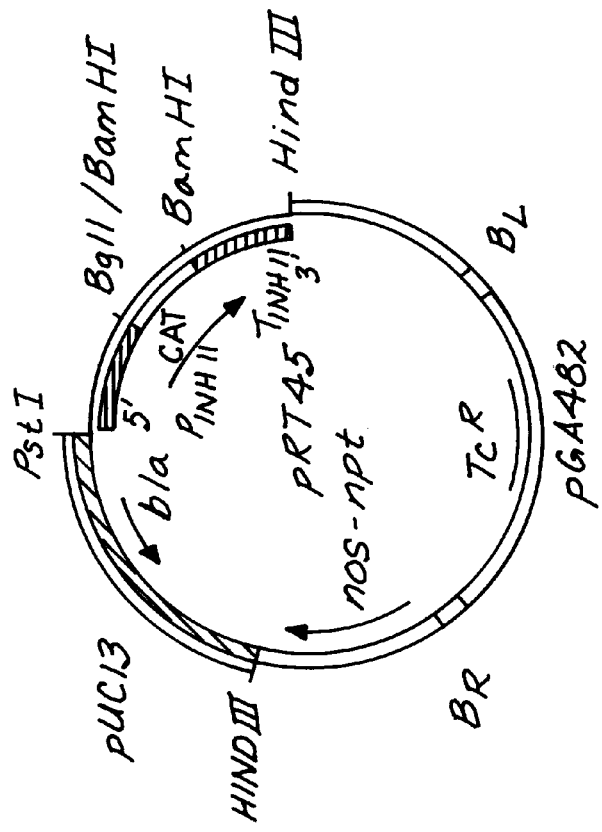
Fig. 7

METHOD OF INDUCING PLANT DEFENSE MECHANISMS

This application is a continuation application based on prior application Ser. No. 07/979,540, filed on Nov. 23, 1992, now abandoned, which is a continuation of International application No. PCT/US91/03685, filed May 24, 1991, which is a continuation-in-part application of U.S. patent application Ser. No. 07/528,956, filed May 25, 1990, now abandoned.

FIELD OF THE INVENTION

This invention relates to methods for inducing plant defense mechanisms. More particularly, this invention relates to methods for inducing the production of plant defense proteins, such as proteinase inhibitors, and to methods of promoting insect, pathogen or viral resistance in plants by inducing the expression of plant defense genes.

BACKGROUND OF THE INVENTION

Damage to crops by insects and other pathogens, including viruses, has resulted in substantial economic losses and decreases in annual agricultural production. Man has created and employed a wide range of pesticidal, fungicidal, bacteriocidal and antiviral chemicals in order to reduce the impact of damage from these biological stresses to food and other plant crops. Although some chemicals have been highly effective in reducing insect damage to valuable agricultural crops, many problems remain from the widespread use of many chemicals which limit their practical utility. For example, chemical application typically provides only transient protection and has to be repeated with varying frequencies depending on such factors as the time of application during the growing season, the life-cycle stage of the target organisms, weather conditions, and the skill, knowledge and expertise of the person applying the chemical treatment. Upon deployment, all organisms in the area are typically exposed to chemical protectants, causing damage to beneficial as well as harmful organisms. In addition, many chemicals are toxic to man and animals, and widespread application has had an adverse impact on the environment.

Other attempts to reduce biological stress damage to crops have included selective plant breeding to obtain genetic expression or amplification of natural resistance characteristics. However, desired overall traits may be under the control of many genes and may be difficult to dissociate from undesired traits. A typical undesired result of desired trait expression or amplification by plant breeding techniques is yield depression—an economically undesirable side effect. Accordingly, a strong need exists for new and improved techniques for obtaining expression of natural resistance characteristics in plant crops.

Signals that are released by attacking organisms, such as plant and fungal cell wall fragments, called oligouronides (plant origin) and β-glucans and chitosans (fungal origins), trigger the activation of a spectrum of defense genes that include proteinase inhibitor proteins. It is the combined expression of several of these genes (depending upon the plant) at once that confers resistance against attacking insects, microorganisms and/or viruses. Research on the direct effects of proteinase inhibitors in plant defense against insects has advanced much faster than research on the other defensive chemicals, and the regulation and expression of the proteinase inhibitor genes has provided a model for studying the expression of all of the genes that code for the defensive chemicals.

Proteinase inhibitor proteins are found throughout all life forms and comprise one of the most abundant classes of proteins in the world. The blood of higher animals, for example, contains cumulatively over 200 mg of various proteinase inhibitor proteins per 100 ml serum (Laskowski, M. Jr. and I. Kato, "Protein Inhibitors of Proteinases," *Ann. Rev. Biochem.* 49: 593–626, 1980). In the plant kingdom most storage organs, such as seeds and tubers, contain from 1–10% of their proteins as inhibitors of various types of proteolytic enzymes (Ryan, C. A., "Proteinase Inhibitors," *The Biochemistry of Plants, A Comprehensive Treatise* (P. K. Stumpf and E. E. Conn, eds), Vol. 6, pp 351–371, Academic Press, New York, 1981), and some fruits contain up to 50% of their proteins as inhibitors of serine endoproteinases (Pearce, G., D. Liljegren and C. A. Ryan, "Proteinase Inhibitors in Wild Tomato Species," *Tomato Biotechnology*, (D. J. Nevins and R. A. Jones, eds) pp 139–144, Alan R. Liss, Inc., New York, 1987). Proteinase inhibitors have been identified for all four classes of proteases (serine, cysteine, metallo- and aspartyl-) and, in the case of serine proteinase inhibitors, several non-homologous families have been isolated and characterized (Laskowski, M. Jr., I. Kato, W. J. Kohr, J. S. Park, M. Tashiro and H. E. Whatley, "Positive Darwinian Selection of Protein Inhibitors of Serine Proteinases," Cold Spring Harbor Symposium in Quantitative Biology, in press).

The functions of the inhibitors in nature appear to be twofold: (1) to prevent uncontrolled proteolysis within cells, organelles or fluids where limited proteolysis is important to biochemical or physiological processes, or (2) to protect proteins of cells, fluids or tissues from foreign proteolytic enzymes. The specific roles of most known proteinase inhibitors, however, are not well understood. This reflects a lack of detailed knowledge about how proteolysis is regulated in many, if not most, processes in nature. Mammalian protein digestion and blood clotting are among the most studied and best understood proteolytic systems (Neurath, H., "Evolution of Proteolytic Enzymes," *Science* 224: 350–363, 1984). The enzymes have been studied for years at the structural and mechanistic levels and more recently at the level of gene regulation. Such extensive detailed information is not available concerning the structure, function and regulation of most other complex proteolytic systems, such as post-translational modification, protein processing, protein turnover, remodeling, etc. (Bond, J. and P. E. Butler, "Intracellular Proteases," *Ann. Rev. Biochem.* 56: 336–364, 1987). Recently, exciting new insights into intracellular protein turnover in procaryotic and eucaryotic cells have revealed roles for ATP, ubiquitin, and calmodulin and calcium in regulating protein degradation. Relationships are being found between the structures of proteins and their half lives in cells, organelles and fluids (Bond, supra; Rechsteiner, M., S. Rogers and K. Rote, "Protein Structure and Intracellular Stability," *TIBS* 12: 390–394, 1987; Dice, J. F., "Molecular Determinants of Protein Half-lives in Eukaryotic Cells," *FASEB J.*, 349–357, 1987). The roles, if any, of proteinase inhibitors in most of these processes are poorly understood.

Neurath, supra, has suggested that, in primitive organisms, control of proteolysis was probably accomplished with proteinase inhibitors. Later, as more complex biochemical and physiological systems evolved, so did complex mechanisms to control proteolytic activity, such as zymogen activation and compartmentation, as well as more refined controls by proteinase inhibitors. Plants appear to have retained vestiges of the primitive control mechanisms for proteolysis. Relatively high levels of proteinase inhibitors are synthesized and stored in plant tissues where they can interact with plant pests or pathogens that attempt to consume them (Ryan, supra). The effects of proteinase inhibitors on insect digestive enzymes was first researched by Birk and her associates in the early 1960s (Ryan, supra). From this and other research in many laboratories over the next 20 years, it became clear that the defensive role of proteinase inhibitors was only a part of a complex interaction between the many defensive chemicals that are present or induced in plants and the predators and pathogens that attack the plants. Plants have been at war with their predators for hundreds of millions of years and have evolved various, and sometimes complex, chemical weapons of defense. This arsenal has included inhibitors of the digestive proteolytic enzymes of the attacking pests (Rhoades, D. F. "Evolution of Plant Chemical Defense against Herbivores," *Herbivores: Their Interaction with Secondary Plant Metabolites* (G. Rosenthal and D. H. Janzen eds) pp 4–55, Academic Press, Inc., New York, 1979).

The digestive processes of higher animals, insects, and microorganisms can vary considerably, both in the classes of the enzymes utilized for protein digestion and in their specificities. Thus, in considering the capability of any proteinase inhibitor in a plant tissue to inhibit a foreign protease, either secreted by a microorganism or released into the digestive tract of a herbivore, the mechanistic class and the peptide bond specificity of the proteinase must be considered as well as structural aspects of the inhibitor that determine its ability to specifically interact with the enzyme (Laskowski, 1980, supra; Laskowski, M. Jr., I. Kato, W. Ardelt, J. Cook, A. Denton, M. W. Empie, W. J. Kohr, J. S. Park, K. Parks, B. L. Schatzley, O. L. Schoenberger, M. Tashiro, G. Bichot, H. E. Whatley, A. Wieczorek and M. Wieczorek, "Ovomucoid Third Domain from 100 Avian Species: Isolation, Sequences, and Hypervariability of Enzyme-Inhibitor Contact Residues," *Biochem.* 26: 202–221, 1987). The association constant of the interaction must be of sufficient magnitude to effectively inhibit the enzyme. Association constants of most protease-inhibitor interactions are from $10^6$M to $10^{10}$M, and sometimes higher (Laskowski, 1980, supra).

Inhibitors of serine proteases have received far more interest than the other classes of proteinase inhibitors. Nature has apparently invented serine endopeptidase inhibitors several times, resulting in at least 13 families, as set forth in the following TABLE 1.

TABLE 1

FAMILIES OF PROTEIN INHIBITORS OF SERINE PROTEINASE

Animals

1. Bovine pancreatic trypsin inhibitor (Kunitz) family.
2. Pancreatic secretory trypsin inhibitor (Kazal) family.
3. Ascaris inhibitor family.
4. Chelonianin family.
5. Serpin family (mechanistically distinct).
6. Hirudin family.

Plants

7. Soybean trypsin inhibitor (Kunitz) family.
8. Soybean proteinase inhibitor (Bowman-Birk) family.
9. Potato I family.
10. Potato II family (Inhibitor II family).
11. Barley trypsin inhibitor family.
12. Squash inhibitor family.

Microbial

13. Streptomyces subtilisin inhibitor (SSI) family.

None of the families shown in TABLE 1 exhibit homology with any other family. All of the inhibitors of serine proteinases employ the same competitive mechanism of inhibition. Researchers in many laboratories over the past 20 years have contributed to the elucidation of the structure, chemistry, and mechanism of action of the serine proteinase inhibitors (Laskowski, 1980, supra; Laskowski, in press, supra). In brief summary, the side chain of the $P_1$ residues of the reactive sites of the inhibitors determine their specificities. It is this residue that the enzyme recognizes as a potential substrate. The $P_1$ residues of the reactive sites of some representative serine proteinase inhibitors are shown in the following TABLE 2.

TABLE 2

REACTIVE SITES OF PROTEINASE INHIBITORS ENCODED BY VARIOUS INHIBITOR GENES OR cDNAs

| GENE | REACTIVE SITES $P_1$—X | SPECIFICITY |
|---|---|---|
| Inhibitor I Family | | |
| TOMATO I | —Leu—Asp— | CHYMOTRYPSIN |
| POTATO I | —Met—Asp— | CHYMOTRYPSIN SUBTILISIN |
| BARLEY C2 | —Met—Glu— | SUBTILISIN |
| Inhibitor II Family | | |
| TOMATO II Domain I | —Arg—Glu— | TRYPSIN |
| POTATO II Domain I | —Arg—Glu— | TRYPSIN |
| TOMATO II Domain II | —Phe—Asn— | CHYMOTRYPSIN |
| POTATO II Domain II | —Leu—Asn— | CHYMOTRYPSIN |
| Bowman-Birk Family | | |
| ALFALFA Domain I | —Arg—Ser— | TRYPSIN |
| ALFALFA Domain II | —Lys—Ser— | TRYPSIN |
| SOYBEAN Domain I | —Lys—Ser— | TRYPSIN |
| SOYBEAN Domain II | —Leu—Ser— | CHYMOTRYPSIN |

When the side chain of the $P_1$ residue enters the specificity pocket of the enzyme, about 200 non-covalent Van der Waals and hydrogen bond contacts, involving just a few amino acids, interact at the interface. The cumulative energy of the interactions virtually freezes the two proteins in a stable complex in which the enzyme cannot complete the hydrolysis of the peptide bond, nor can the complex easily dissociate.

The presence of a small percentage of the total dietary proteins as serine proteinase inhibitors can have severe effects on the digestive physiology of animals, including insects. In laboratory animals, trypsin inhibitors can reduce the effective concentration of trypsin that is available to the animal for digestion. This, in turn, lowers the effectiveness of trypsin to activate other proenzymes secreted by the pancreas. Additionally, the trypsin-inhibitor complexes can trigger feedback mechanisms that signal the pancreas to trigger an overproduction of digestive enzymes, while signaling the stomach and brain to reduce the desire of the animal to eat. Prolonged feeding on the inhibitors can lead to the inability to derive amino acids from food as well as the inability to recycle essential amino acids present in the secreted digestive enzymes.

Studies of the effects of dietary proteinase inhibitors on the growth and development of insects, either artificially introduced into defined diets or already in plant tissues, have shown that the native inhibitors can be detrimental to the growth and development of insects from a variety of genera including Heliothis, Spodoptera, Diabiotica and Tribolium (Ryan, supra; Broadway, supra; Rechsteiner, supra). This anti-nutrient property is probably enhanced by, or enhances, other anti-nutrient or toxic chemicals that are part of the array of defensive chemicals of plants. The proteinase inhibitors, while not having an intrinsically high toxicity, therefore provide a set of genes with which to transform plants to study both fundamental and applied aspects of plant defense against herbivores and pathogens.

The large numbers of known, naturally-occurring proteinase inhibitors encompass a wide range of inhibitor specificities. Extensive studies of the relationships of the structures at the reactive sites of avian ovomucoids (serine proteinase inhibitors) from 100 species have revealed that 8 of the 11 amino acids that are involved with the contacts between serine proteinases and their inhibitors are hypervariable (Laskowski, 1987, supra), that is, these amino acids are mutating faster than the rest of the amino acids of the inhibitors. In enzymes, the opposite situation occurs. The active site residues do not mutate as fast as residues that are not involved in the enzyme action. The evidence indicates that some environmental pressures are directing this hypervariability (Laskowski, 1987, supra). One possibility for this phenomenon may be that a natural selection of proteinase inhibitor specificities has taken place in response to a changing spectrum of proteinases of attacking predators and pathogens.

In addition to naturally-occurring proteinase inhibitors, several serine proteinase inhibitor genes and/or cDNAs have recently been isolated and used to transform plants with foreign proteinase inhibitor genes to confer their defensive capabilities. For Example, European patent application Publication No. 0272144 and Hilder, V. A., et al., "A Novel Mechanism of Insect Resistance Engineered into Tobacco," *Nature* 330:160–163 (1967), disclose a cDNA coding for a cowpea trypsin inhibitor (CpTI) fused with a constitutive CaMV promoter and a nopaline synthase terminator, and the use of the construct to transform tobacco plants. The CpTI trypsin inhibitor was constituitively expressed in the leaves of transformed plants. The transformed plants were said to exhibit a resistance toward *Heliothis virescens,* the tobacco bud worm, which is an insect pest that ordinarily thrives on tobacco leaves. Sanchez-Serrano, J. J., et al., "Wound-Induced Expression of a Potato Inhibitor II Gene in Transgenic Plants," *EMBO J* 6:303–306 (1987) discloses transformation of tobacco plants with a wound-inducible potato Inhibitor II gene.

Activation of defensive genes in plants by pathogen and herbivore attacks, or by other mechanical wounding, can result from the action of a variety of signaling molecules that are released in complex temporal patterns following the initial invasion of the tissues (see Darvill, A. G. and P. Albersheim, *Ann. Rev. Plant Physiol.* 35:243–275, 1984; M. A. Lawton and C. J. Lamb, *Mol. Cell. Biol.* 7:335–341, 1987; and C. A. Ryan, *Ann. Rev. Cell Biol.* 3:295–317, 1987). Transport of these signals is mediated locally through intercellular and intracellular fluids that permeate wound or infection sites (Green, T. R. and C. A. Ryan, *Science 175:776–777, 1972*) or travel systemically through the vascular system of the plants (Kuc, J. and C. Presisig, *Mycologia* 76:767–784, 1984; M. Kopp, et al., *Plant Physiol.* 90:208–216, 1990; and K. E. Hammond-Kosack, et al., *Physiol. Mol. Plant Path.* 35:495–506, 1989). Limited indirect evidence has indicated that signaling may also occur through the atmosphere (Baldwin, I. T. and J. C. Schultz, *Science* 221:277–279, 1983); D. F. Rhoades in *Plant Resistance to Insects,* P. Hedin, ed., American Chemical Society, Washington, D.C., 1983; and H. J. Zeringue, *Phytochemistry* 26:1357–1360, 1987). Whereas several chemicals, including ethylene, have been identified as candidate intracellular signaling molecules for inducible defense genes, no direct biochemical evidence has been presented in the art that would implicate any volatile chemicals besides ethylene as signals that can active plant defensive genes. Ethylene is highly selective in activating defensive genes and only activates chitinase synthesis. Ethylene does not activate the syntheses of other defensive chemicals shown in Table 1 and therefore is not part of the general mechanism for activating defensive genes in plants.

The chemical structure of jasmonic acid is similar to the prostaglandins, important signaling molecules in animals (Samuelson, B. et al., *Ann. Rev. Biochem.* 47:997–1029, 1978). Jasmonic acid is apparently synthesized from linolenic acid, a fatty acid ubiquitous in plants (Vick, B. A. and D. C. Zimmerman, *Plant Physiol.* 75:458–461, 1984; and J. M. Anderson in *Second Messengers in Plant Growth and Development,* Alan R. Liss, Inc., pp. 181–212, 1989). The release of linolenic acid or 3,6,9,12-octadecatetraenoic acid, triggered by the activation of specific lipases in response to pest or pathogen attacks, could lead rapidly to the production of jasmonic acid or methyl jasmonate through the action of enzymes present in the plants. Jasmonic acid may then act as a second messenger molecule in signal transduction pathways leading to defensive gene expression.

Previous studies have shown that methyl jasmonate, or jasmonic acid, when applied directly to plants can produce a variety of responses including growth inhibition (Dalther, W., et al., *Planta* 153:530–535, 1981); and J. Yamane, et al., *Plant and Cell Physiol.* 22:689–697, 1981), the promotion of senescence and/or abscission (Ueda, I. et al., *Plant Physiol.* 66:246–249, 1980; and Curtis, R., *Plant Growth Regulators* 3:157–168, 1984) as well as the induction of specific leaf proteins in monocots and dicots (Mueller-Uri, J., et al., *Planta* 176:241–247, 1988; J. M. Anderson, et al, *Plant Science* 62:45–52, 1989; and P. E. Staswick, *The Plant Cell* 2:1–6, 1990). There has been no suggestion in the art, however, that jasmonate derivatives could be involved in plant predator defense mechanisms.

In potato and tomato leaves, two small wound-inducible gene families of serine proteinase inhibitors have been identified (Lee, J. S. et al., *Proc. Natl. Acad. Sci. USA* 83:7277–7281, 1986; and, Cleveland, T. E. et al., *Plant Mol. Biol.,* in press). From wound-inducible mRNAs coding for the two families of inhibitors, cDNAs have been isolated (Graham, J. et al., *J. Biol. Chem.* 260:6555–6560, 1985; and, Graham, J. et al., *J. Biol. Chem.* 260:6560–6564, 1985) and utilized as probes to identify the wound-inducible genes in potato and tomato gene libraries (Lee et al., supra. and Cleveland et al., supra). 5' Flanking sequences to the wound-inducible potato inhibitor IIK gene have been operably-linked to give wound-inducible expression of chloramphenicol acetyltransferase (CAT) in transgenic tobacco plants (Thornburg et al., *Proc. Natl. Acad. Sci. USA* 84:744–748, 1987). However, there has been no suggestion in the art that jasmonate derivatives could be used to induce expression of a foreign gene operably-linked to such a wound-inducible 5' regulatory sequence.

SUMMARY OF THE INVENTION

It has now been discovered that the expression of plant predator defense proteins and foreign genes operably linked to a wound-inducible 5' regulatory sequence is induced in plant tissue by contacting plants to be treated with a defense protein inducing agent. The inducing agent, which may be jasmonic acid, lower alkyl esters of jasmonic acid or jasmonic acid-like derivative compounds, induces the expression of genes in the plants resulting in the production of defense proteins, such as proteinase inhibitors, thionins, chitinases and β-glucanases. Plants may be contacted with the inducing agent by direct application to plant tissue or by airborne transmission of the inducing agent. Extremely small quantities of the inducing agent have been found to be effective in inducing defense protein expression, and accordingly, are effective in reducing the biological stress of predator attack in treated plant crops.

BRIEF DESCRIPTION OF THE DRAWINGS

FIG. 6 is the nucleotide sequence (SEQ ID NO. 1) of the wound-inducible potato protease inhibitor IIK gene also showing the sequence in the 5' flanking regions containing the 5' regulatory nucleotide sequence elements, e.g., the promoter.

FIG. 7 is a graphic presentation of a vector containing the foreign chloramphenicol acetyltransferase (CAT) gene ligated to the wound-inducible potato protease inhibitor IIK gene 5' regulatory nucleotide sequence.

DETAILED DESCRIPTION OF THE REPRESENTATIVE EMBODIMENTS

Figure 1:
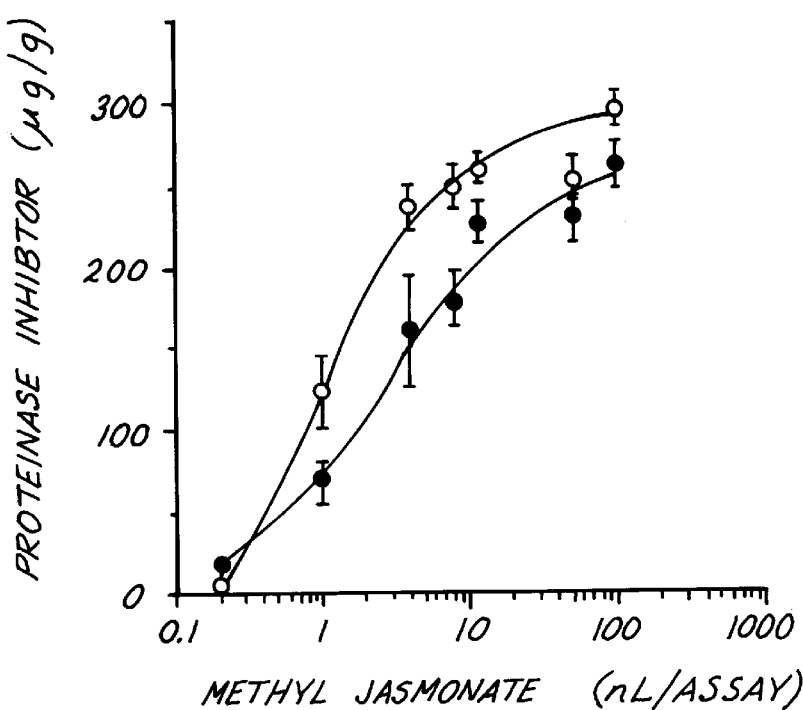
FIG. 1 is a graphic representation of the induction of proteinase Inhibitor I and II proteins in the leaves of tomato plants in response to varying concentrations of airborne methyl jasmonate.

In accordance with the present invention, plants capable of producing predator defense proteins are treated by contacting the plants with an amount of a defense protein inducing agent effective to induce production of defense proteins by the plants. The method Is also useful for inducing production of a foreign protein by a transgenic plant with a genome having a wound-inducible defense protein gene 5' regulatory nucleotide sequence operably linked to a foreign gene.

As used herein, the term "protein encoding nucleotide sequence" is intended to include nucleotide sequences in DNA or RNA capable when transcribed or translated, respectively, of giving rise to an amino acid sequence of greater than three amino acids in length, e.g., predator defense proteins, defense proteins, or a foreign gene.

As used herein, the term "defense protein inducing agent" is intended to include agents inducing expression of predator defense proteins and wound-inducible proteins, e.g., methyl jasmonate.

As used herein, the term "foreign gene" is intended to include genes which are not commonly found in nature in the genome of the plant cell and includes eukaryotic and prokaryotic genes and their derivatives prepared by recombinant methods.

As used herein, the terms "wound inducible 5' regulatory nucleotide sequence", "5' regulatory nucleotide sequence", "5' regulatory region", "defense gene regulatory sequences", "5' regulatory sequences", and "5' flanking (regulatory) region" are used synonymously to include the nucleotide sequences residing 5' to a defense protein gene and which are capable of inducing expression of the downstream nucleotide sequences when the plant is exposed to a defense protein inducing agent, e.g., methyl jasmonate.

As used herein, the term "operably linked" is intended to include the joining of one nucleotide sequence to another so that the desired effect is obtained, e.g., joining in the correct reading frame for an open reading frame (ORF); or joining a non-translated region to an ORF or another non-translated region in such a manner that the desired regulatory effect (positive up regulation or negative down regulation) is obtained in response to the defense protein inducing agent.

As used herein, the terms "predator defense proteins" and "defense proteins" are used synonymously to include proteins which impede plant tissue attack or ingestion by predators, such as by insects, fungi, bacteria or viruses, and thereby increase the resistance of plants to predator attack. The defense proteins may act directly to impede plant tissue attack or ingestion, or may act indirectly, such as, for example, as enzymes that produce other defense compounds from precursor materials, enzymes that are part of a biological pathway that leads to the synthesis of defense compounds from precursor materials, or proteins that regulate an enzyme or enzymes that lead to the synthesis of defense compounds. Representative examples of defense proteins that act directly include proteinase inhibitors, thionins, chitinases and β-glucanases. Representative enzymes that lead to the synthesis of defense compounds include, for example, casbene synthase. Representative enzymes that are part of a biosynthetic pathway leading to the formation of defense compounds include, for example, enzymes in the phenylpropenoid and terpenoid pathways which lead to the synthesis of phytoalexin antibiotics, alkaloids and other toxic chemicals. Other types of predator defense proteins useful in connection with the invention disclosed herein will, of course, be apparent to those skilled in the art. Particularly suitable predator defense proteins include inhibitors of the digestive proteolytic enzymes of the attacking predator, such as proteinase inhibitors, and other proteins that have defensive properties against insects, fungi, bacteria or viruses. Representative proteinase inhibitor defense proteins inducible by the present Invention include, for example, the Kunitz family trypsin inhibitors, the Bowman-Birk family proteinase inhibitors, the Inhibitor I family proteinase Inhibitors, the Inhibitor II family proteinase inhibitors, the barley family trypsin inhibitors, and the the squash family proteinase inhibitors. Plants to be treated in accordance with the invention may either be capable of naturally expressing predator defense proteins in response to predator attack (i.e., tissue wounding) or may be genetically engineered to express defense proteins under the control of a suitable inducible promoter, as will be apparent to those skilled in the art.

Defense protein inducing agents useful in the practice of the invention include compounds or compositions capable upon contact with plant tissue of inducing the expression of a protein encoding nucleotide sequence, e.g., predator defense proteins or foreign genes operably-linked to a defense protein 5' regulatory region. Suitable defense protein inducing agents include agents comprising a compound of the formula:

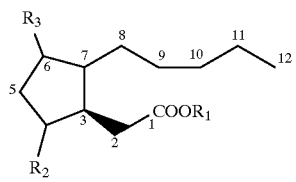

wherein $R_1$ is H, lower alkyl having from 1 to 6 carbon atoms or a carrier ligand; $R_2$ and $R_3$ are independently selected from H, —OH, O or lower alkyl having from 1 to 6 carbon atoms; and the agent is optionally single or double bonded at one or more of the $C_2$:$C_3$, $C_3$:$C_4$, $C_3$:$C_7$, $C_4$:$C_5$, $C_5$:$C_6$, $C_6$:$C_7$, or $C_9$:$C_{10}$ bonds. Suitable carrier ligands include moieties capable of delivering the inducing agent to plant cells without Interfering with the inducing activity of the agent, such as, for example, mono- or polysaccharides, amino acids, polypeptides having from 1 to 500 amino acid residues or more, and the like. Preferably, the carrier ligands will be capable of being clipped from the remainder of the inducing agent by the natural biological activity of the plant cell. Representative defense protein inducing agents include jasmonic acid, 7-iso-jasmonic acid, 9,10-dihydrojasmonic acid, 2,3-didehydrojasmonic acid, 3,4-didehydrojasmonic acid, 3,7-didehydrojasmonic acid, 4,5-didehydrojasmonic acid, 5,6-didehydrojasmonic acid, 6,7-didehydrojasmonic acid, 7,8-didehydrojasmonic acid, and the lower alkyl esters, the carrier ligand conjugates and the stereoisomers thereof. Presently preferred defense protein inducing agents are jasmonic acid and methyl jasmonate.

Amounts of the inducing agent effective to induce the expression of a protein encoding nucleotide sequence (e.g., defense proteins, such as proteinase inhibitors, or foreign genes operably-linked to defense gene regulatory sequences), in treated plants will depend on many factors including the nature, environment and condition of the plants to be treated, the method of contact of the inducing agent with plant tissue to be treated and other factors. For example, plant tissue may be treated in accordance with the invention by contacting the tissue with a solution comprising the inducing agent. Alternatively, plant tissue may be treated by supplying a volatile source of the inducing agent in the vicinity of the plant tissue and allowing the agent to diffuse to the plant tissue through the atmosphere.

When employed in solution form, plant tissue to be treated may be contacted with a solution comprising an amount of the inducing agent effective to induce the expression of defense proteins by the treated plant. In one embodiment, the solution may be an aqueous solution comprising from about 1 µg/ml to about 100 mg/ml of the inducing agent, more preferably from about 1 ng/ml to about 10 mg/ml of the inducing agent, and most preferably from about 1 µg/ml to about 1 mg/ml of the inducing agent. Alternatively, the solution may comprise an organic solvent, such as glycerol. The solution may be applied directly to plant tissue to be treated, such as by spraying the solution onto the plant tissue, or by drenching or otherwise contacting the plant tissue with the solution.

When plant tissue is to be treated through the airborne transmission of the inducing agent, a volatile source of the inducing agent is placed in the vicinity of the plant tissue and the agent is allowed to diffuse or disperse through the atmosphere to contact the plant tissue. In this embodiment, the volatile source may be, for example, plant materials which naturally produce the inducing agent or a volatile solution of the agent, such as a solution comprising a volatile organic solvent and the inducing agent. Suitable organic solvents for this purpose include methanol, ethanol and other volatile organic solvents. The solvent may also be water. The manner in which the volatile source of the inducing agent is placed in the vicinity of the plant tissue to be treated is not critical to the practice of the invention. For example, the inducing agent may be placed in an open container in the vicinity of the plant tissue, on a matrix support, such as a fiber matrix, in the vicinity of the plant tissue, or may be applied directly to the soil in the vicinity of the plant tissue.

Inducible defensive responses in plants are known to be activated both locally and systemically by signaling molecules that are produced at sites of pathogen or insect attacks, but only one chemical signal, ethylene, has been known in the art to travel through the atmosphere to activate plant defensive genes. However, as will be more fully demonstrated in connection with the following examples, defense protein inducing agents as described herein, when applied to surfaces of plants, induce the synthesis of a protein, e.g., defense proteins in the treated plants (and in nearby plants), or foreign proteins operably-linked to defense protein 5' regulatory sequences (e.g., a promotor region). The presence of the inducing agent in the atmosphere of chambers containing plants also results in the accumulation of defense proteins (or foreign proteins) in leaves of the plants. In addition, when sagebrush, a plant shown to possess methyl jasmonate in leaf surface structures, is incubated in chambers with plants, defense protein accumulation is induced in the leaves of the plants, demonstrating that interplant communication occurs from leaves of one species of plant to leaves of another species to activate the expression of defensive genes.

The foregoing may be better understood in connection with the following representative examples, which are presented for purposes of illustration of presently preferred embodiments of the invention.

Example 1

Accumulation of Proteinase Inhibitor I in Tomato Leaves Induced by Methyl Jasmonate A solution of methyl jasmonate ($10^{-3}$ M in water containing 0.125% (v/v) Triton X-100) was sprayed on the upper leaves of intact, 14 day old tomato plants. Control plants were sprayed with an aqueous solution of 0.125% (v/v) Triton X-100 lacking methyl jasmonate. The treated and control plants were allowed to dry in the open at room temperature for 30 minutes and then placed in sealed plexiglass boxes (11.34 L capacity) and incubated under constant light (300 µE $m^{-2}$ $sec^{-1}$) for 24 hours. Chamber A contained both methyl jasmonate sprayed plants and control plants. Chamber B contained control plants together with plants that had been wounded once across their lower leaves with a haemostat at the same time that the plants were sprayed. Proteinase Inhibitor I levels were assayed by radial immunodiffusion assays according to the procedure of Ryan, C., *Anal. Biochem.* 19:434–429, 1967 and R. Trautman, et al., *Immunochemistry* 8:901–916, 1971. The results are shown in the following Table 3:

TABLE 3

| | Proteinase Inhibitor I (μg/g tissue)* |
|---|---|
| Chamber A: | |
| Methyl Jasmonate Sprayed Plants | 210 +/− 7 (n = 6) |
| Control Plants | 28 +/− 3 (n = 6) |
| Chamber B: | |
| Wounded Plants | 86 +/− 8 (n = 4) |
| Control Plants | 0 (n = 6) |

*Values reported with standard error.

As can be seen from Table 3, an aqueous solution of methyl jasmonate when sprayed on leaves of tomato plants powerfully induces the synthesis and accumulation of proteinase Inhibitor I protein. The chemical induced an accumulation of Inhibitor I that was significantly higher than could be induced by wounding. As further shown in Table 3, control plants that had not been sprayed with methyl jasmonate, but incubated in the same chamber with the sprayed plants, accumulated low levels of proteinase Inhibitor I protein. Control plants incubated in a separate chamber did not accumulate Inhibitor I at all. These results demonstrate that volatile methyl jasmonate induced the synthesis of proteinase inhibitors in the untreated control plants.

Example 2

Induction of Proteinase Inhibitor I and U in Tomato by Methyl Jasmonate

Tomato plants were placed in air-tight chambers together with cotton-tipped wooden dowels onto which various dilutions of methyl jasmonate in ethanol had been applied to the cotton. The dowels were placed so that no interaction was possible between the methyl jasmonate and the plants except through the atmosphere. After incubating the plants in light for 24 hours following the introduction of methyl jasmonate to the chambers, leaf juice from the plants was assayed for Inhibitor I and II protein levels by immunoradial diffusion as in Example 1. As shown in FIG. 1, wherein the open circles represent Inhibitor I and the closed circles represent Inhibitor II, the presence of volatile methyl jasmonate in the chambers resulted in the synthesis and accumulation of both proteinase Inhibitors I and II in a dose dependent manner. Half maximal accumulation of both inhibitors was observed when 1 to 2 nL (nanoliters) of methyl jasmonate was present on the cotton wicks in the chambers. The dose dependency of the accumulation of inhibitors indicates that the leaves must be rapidly absorbing the volatilized methyl jasmonate. Below about 10 nL of methyl jasmonate per chamber the leaves were not maximally induced. This suggests that at these lower concentrations the volatile methyl jasmonate levels were limiting and that leaves were not able to assimilate enough of the molecules to maximize the signaling responses. Above 10 nL per chamber, volatile methyl jasmonate appeared to be at high enough concentrations in the chambers to be assimilated at levels that could maximally induce the inhibitors.

Example 3

Induction of Inhibitor I and II in Tomato Plants

The induction of proteinase Inhibitor I and II proteins in the leaves of intact tomato plants after exposure to airborne methyl jasmonate was further evaluated as follows. Two-week-old tomato plants were placed in 1250 ml air-tight glass chambers together with cotton-tipped wooden dowels to which had been applied 1 μL of dilutions of (+/−)-methyl jasmonate in ethanol. The cotton tip was placed approximately 4–6 cm from the plant leaves. The jars were incubated in constant light as in Example 1 at 28° C. for 24 hours. Leaf juice was analyzed for proteinase Inhibitors I and II. The results are shown in FIG. 2, in which the bars indicate the standard error (n=4).

Figure 2:
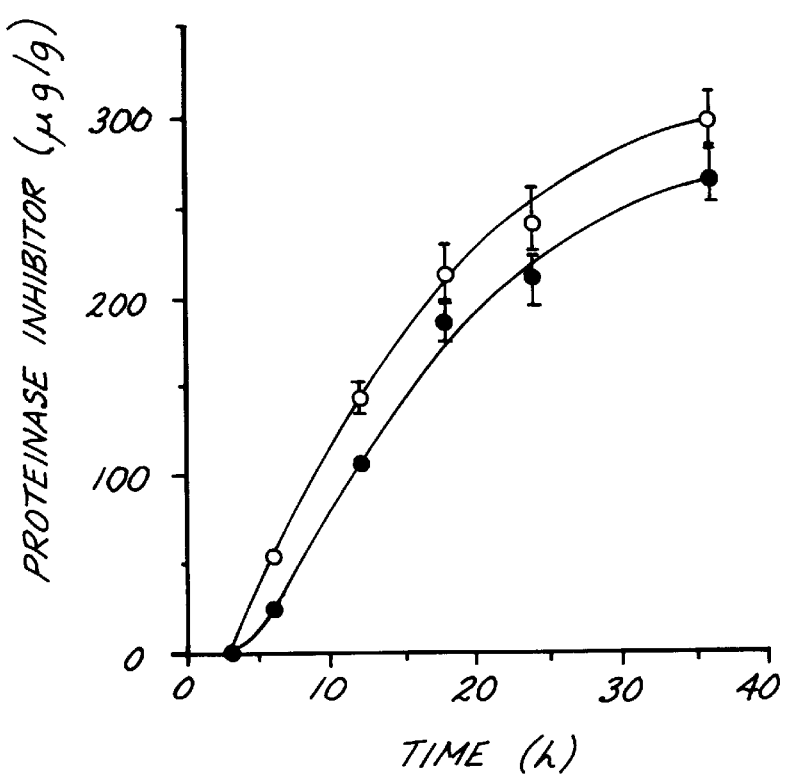
FIG. 2 is a graphic representation of the time course of induction of proteinase Inhibitor I and II proteins in the leaves of tomato plants in response to airborne methyl jasmonate.

Referring to FIG. 2, when methyl jasmonate was present in the chambers at saturating levels (100 nL/chamber), tomato plants began to accumulate proteinase Inhibitor I (open circles) and II (closed circles) at about 5 hours after the initial exposure to the volatile compound and continued to accumulate the proteins at linear rates for nearly 20 hours. After about 20 hours, however, the rate of accumulation of the two inhibitors declined. The reasons for this are not yet apparent. Following wounding, the rates of accumulation of the proteinase inhibitors have been shown to decline after about 10 hours, but the wound induction could be reinforced by a wound administered about 12 hours after the initial wound (Graham, J. S., G. Hall, G. Pearce and C. A. Ryan, *Planta* 169: 399–405, 1986. The constant presence of the methyl jasmonate vapor may have simply fatigued the system, or the leaves may simply have absorbed all of the methyl jasmonate and converted it to a non-active product.

The levels of both proteinase Inhibitors I and II that accumulate in response to methyl jasmonate are higher than those found in tomato leaves in response to either wounding (Graham, et al., supra) or oligouronide elicitors (Walker-Simmons, M., L. Hadwiger and C. A. Ryan, *Biochem. Biophys. Res. Comm.* 110:194–199, 1983). This suggests that the methyl jasmonate may be entering the signal transduction network very efficiently and is bypassing some biochemical constraints that limit the wound-inducible induction of the proteinase inhibitors.

Example 4

Induction of Proteinase Inhibitor I in Tomato by Methyl Jasmonate

The synthesis of proteinase Inhibitor I protein in response to increasing times of exposure of tomato plants to airborne methyl jasmonate was determined by incubating tomato plants in air-tight 1250 ml glass chambers in the presence of volatile methyl jasmonate (100 nL dissolved in 1 ml ethanol) pipetted onto cotton swabs. At various times following exposure to methyl jasmonate vapors, the plants were transferred to chambers free of methyl jasmonate and further incubated for a total of 24 hours after the initial exposure, when leaf juice was assayed for proteinase Inhibitor I content in accordance with the procedure of Example 1. The results are shown in FIG. 3, in which bars show the standard error (n=4).

Figure 3:
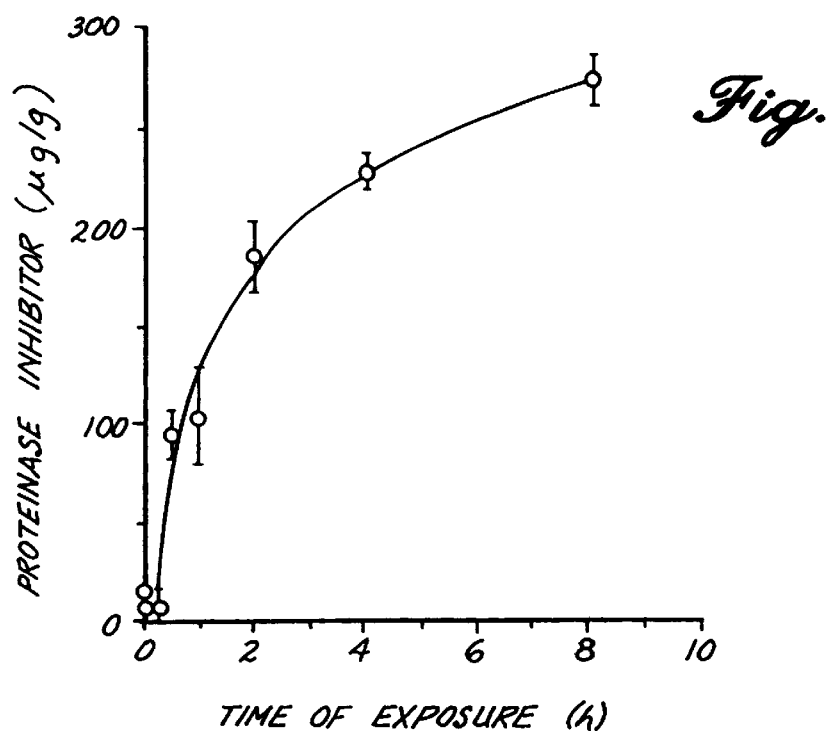
FIG. 3 is a graphic representation of the induction of proteinase Inhibitor I and II proteins in tomato plants in response to varying times of exposure to airborne methyl jasmonate.

As shown in FIG. 3, exposure of tomato plants for only 30 minutes to methyl jasmonate volatiles originating from a 100 nL of the chemical per chamber, was sufficient to induce a moderate level of accumulation of proteinase inhibitor protein. With increasing exposure to the volatile methyl jasmonate the accumulation of inhibitor protein increases and approaches a maximum at about 8 hours.

Example 5

Induction of TTI and ATI in Tobacco and Alfalfa Plants

To determine if methyl jasmonate can activate proteinase inhibitors in other plant genera including another plant family, small tobacco plants (Xanthi) and small alfalfa plants (cultivar RA3) were exposed to volatile methyl jasmonate (100 nL methyl jasmonate per chamber) and leaf juice was assayed for the presence of tobacco trypsin inhibitor (TTI) and alfalfa trypsin inhibitor (ATI) (Brown, W. and C. A. Ryan, *Biochemistry* 23:3418–3422, 1984) by radial immunodiffusion as described in Example 1. In the presence of methyl jasmonate, TTI levels were elevated from 7±3 $\mu$g/g tissue (n=4) in leaves of control plants to 116±37 $\mu$g/g tissue (n=4) in leaves of plants exposed to methyl jasmonate. ATI levels were elevated from 33±7.3 $\mu$g/g tissue (n=4) in control plants to 385±26.5 $\mu$g/g tissue (n=4) in exposed plants. Thus, airborne methyl jasmonate induces the expression of several proteinase inhibitor genes representing three inhibitor families in leaves of plants from both the Solanaceae and Fabaceae families.

Example 6

Induction of Inhibitor I and II in Tomato by Cohabitation with Sagebrush

To demonstrate that a species of plant that contained methyl jasmonate in its leaves could induce expression of proteinase inhibitor genes in nearby plants, 15-day-old tomato plants (approximately 5 cm in height and having three expanding leaves) were placed in air-tight 1250 ml glass chambers together with samples of the sagebrush *Artemisia tridentata Nutt.* subsp. *tridentata* (approximately 10 cm branches having several dozen leaves; branches had an average weight of 4.5±0.5 g). The plants were placed so that no physical contact was possible between the sagebrush leaves and tomato leaves. The chambers were sealed and incubated for two days under the conditions described in Example 1. Control tomato plants were placed in separate chambers in the absence of sagebrush and incubated under identical conditions. Following incubation, leaves of the tomato plants were assayed for proteinase Inhibitors I and II proteins by radial immunodiffusion as described in Example 1.

Plants for experiment 1 were collected from one mile East of Desert Aire, Wash. (Location I). Plants for experiments 2 and 3 were collected from Lyons Ferry, Wash. (Location 2).

The results are shown in the following Table 4:

TABLE 4

| | Proteinase inhibitors $\mu$g/g tissue | |
|---|---|---|
| | I | II |
| Experiment I: | | |
| Plants incubated with *A. tridentata* (Location 1) | 54.5 +/− 8.7 (n = 4) | n.d. |
| Controls | 0 (n = 4) | n.d. |
| Experiment II: | | |
| Plants incubated with *A. tridentata* (Location 2) | 71.0 +/− 16.1 (n = 10) | 50.6 +/− 13.7 (n = 12) |
| Controls | 0 (n = 10) | 0 (n = 12) | n.d., not determined.

As shown in Table 4, within two days the leaves of the tomato plants exhibited elevated levels of both proteinase Inhibitors I and II.

Figure 4A:
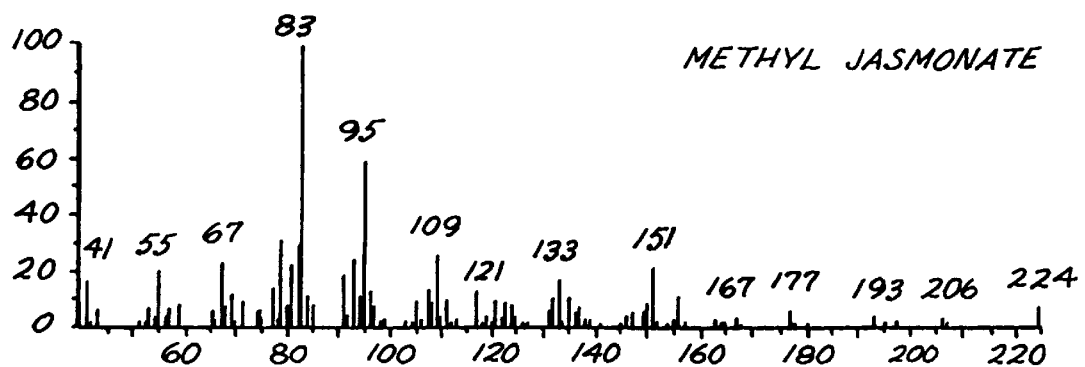
FIG. 4 is the mass spectra of methyl jasmonate isolated from *Artemisia tridentata* ssp. *tridentata* compared with a sample of authentic methyl jasmonate.
Figure 4B:
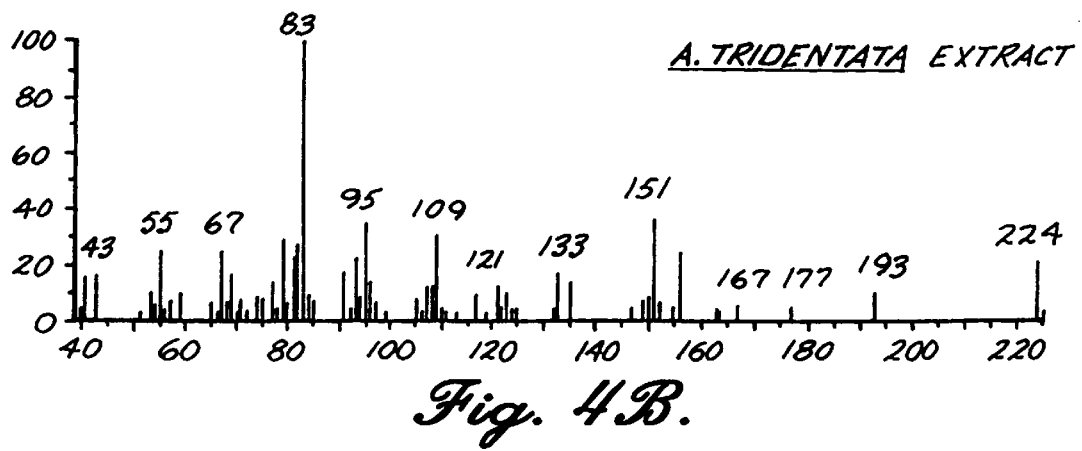

Cotton swabs were brushed across the leaf surfaces of *A. tridentata* leaves and placed in glass chambers with tomato plants, similar to the experiments described previously with methyl jasmonate. A volatile component induced the accumulation of proteinase inhibitors in the leaves (data not shown). To determine if methyl jasmonate was actually present in the leaf surface trichomes of *A. tridentata*, an ethanolic fraction from the leaf surface was obtained and fractionated into its components by silica gel column chromatography, thin layer chromatography and reverse phase HPLC, as follows. The terminal 15 cm of *A. tridentata* branches were collected from a natural population growing at Lyons Ferry, Wash. Branches (1 Kg) containing several hundred small leaves were agitated in ethanol (1 L) for 10 seconds. The resultant mixture was concentrated to a brown oil (2.4 ml) which was extracted into pentane (75 ml). The pentane was removed by rotary evaporation and the resultant yellow oil (1.2 ml) fractionated on a Silica gel (Silicar, Mallinckrodt, 60A) column (1.2×20 cm). The column was first washed in pentane. The ethyl acetate content of the pentane was increased in 5% (v/v) steps to 10% (v/v) then in 10% steps to 100% ethyl acetate. A fraction containing volatile proteinase inhibitor inducing activity eluted in 30% (v/v) ethyl acetate. This fraction was further resolved by preparative thin layer chromatography on silica gel. The plate was developed in benzene-ethyl acetate (10:1, v/v). Compounds migrating with an Rf of 0.38 exhibited proteinase inhibitor inducing activity when exposed to young tomato plants. This active material was further chromatographed on an analytical silica gel thin layer (Kodak) sheet which had been pre-soaked in 5% (w/v) silver nitrate in 75% (v/v) methanol. Before chromatography the plate was allowed to dry for 20 hours at 28° C. The plate was chromatographed in 30% (v/v) ethyl acetate in hexanes. Proteinase inhibitor inducing activity was found associated with components that migrated at an Rf of 0.17. This material was further resolved by reverse phase HPLC on a Beckman Ultraphase C18 ion pair column (4.6×250 mm, 5 mm) in 50% acetonitrile: 0.1% trifluoroacetic acid in water. The column was developed isocratically. A partially resolved double peak was resolved that contained the proteinase inhibitor activity. Gas chromatography/mass spectroscopy of the compounds was carried out on a Hewlett Packard 5985 GC/MS system. The column was a Superox FA (Alltech, 30 m×0.25 mm) with He carrier gas at 1.4 Kg cm$^{-2}$. The column temperature was 45° C. for 5 minutes then increased at 10° C./minute to 200° C. which was held for 10 minutes. Two compounds with identical GC retention times and similar mass spectra to methyl jasmonate were found in all biologically active fractions. The mass spectrum of one of these compounds was compared to that of authentic methyl jasmonate, as shown in FIG. 4. These results demonstrate that the airborne chemical signal from *A. tridentata* leaves that induces the expression of the proteinase inhibitor genes is methyl jasmonate.

The ability of methyl jasmonate to activate at least four elicitor- and wound-inducible genes from two plant families indicates that this compound has general properties to activate a wide spectrum of plant defensive genes. Methyl jasmonate molecules may enter the vascular system via stomates and activate the proteinase inhibitor genes through a receptor-mediated signal transduction pathway. Alternatively, methyl jasmonate may diffuse into the leaf cell cytoplasm where it would be hydrolysed to jasmonic acid by intracellular esterases. The free acid may, in turn, be an integral part of a general signal transduction system that regulates inducible defensive genes in plants. The data herein demonstrate that a highly sensitive mechanism is present in plants that can activate defense protein genes in response to defense protein inducing agents. The mechanism is believed to be broadly present in nature. It has been further demonstrated herein that interplant defense signaling can occur between two distantly related plant families, with a representative inducing agent, volatile methyl jasmonate, as the signaling molecule.

Example 7

To determine if methyl jasmonate could induce expression of a foreign gene, a transgenic plant was reconstructed with a 5' regulatory region from a defense protein gene operably-linked to a foreign chloramphenicol acetyl transferase (CAT) gene. The potato Inhibitor II gene was cloned, the nucleotide sequence of the gene and its 5' flanking (regulatory) sequences was determined, and vectors constructed wherein the regulatory sequences control expression of CAT. Tobacco cells were transduced with these vector gene sequences and the resultant transgenic plant leaves were tested for methyl jasmonate induction of CAT gene expression.

Screening of a Library of Potato Genes for Inhibitor II Genes

To clone the Inhibitor II gene, about $3.5 \times 10^5$ plaques in a Russet Burbank potato genomic library (that was a gift of David Anderson, Phytogen, Pasadena, Calif.) were screened by using nick-translated tomato inhibitor II cDNA as a probe. *Escherichia coli* strain K802 (hsr$^-$, ham$^+$, lac$^-$, gal$^-$, met$^-$) was used as the host. Nitrocellulose plaque lifts of the library were prehybridized at 55° C. in a solution containing 5x Denhardt's solution, 5x SSPE, 0.1% NaDodSO$_4$, denatured salmon sperm DNA (100 μg/ml), and poly(A)$^+$ RNA (1 μg/ml) (Maniatis et al. In: *Molecular Cloning: A Laboratory Manual* (Cold Spring Harbor Laboratory, Cold Spring Harbor, N.Y. 1982). For the hybridization step, 0.1 μg of boiled nick-translanted inhibitor II cDNA was added to the mixture and incubated at 55° C. for 10 hr. Methods for washing, drying and autoradiography of blots were performed as described (Maniatis et al., supra). Twenty-nine plaques containing DNA that hybridized strongly with the probe were selected, amplified, and screened three additional times to ensure purity of the clone. DNA was isolated from the amplified clones for restriction nuclease digestion, Southern analysis, and subcloning of restriction fragments.

Figure 5:
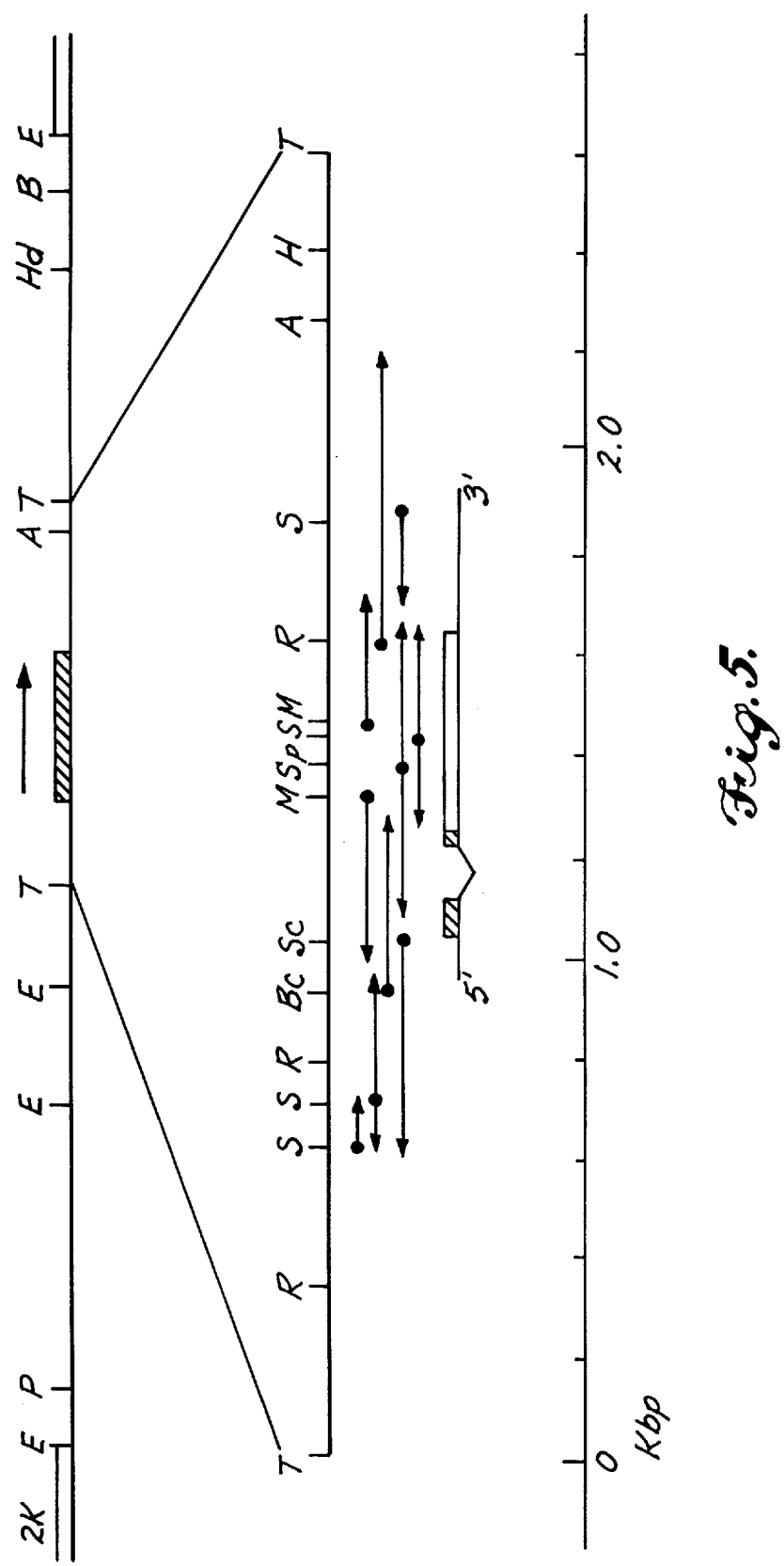
FIG. 5 is a graphic presentation of the restriction map of the potato protease inhibitor IIK gene.

A clone called inhibitor IIK containing an 8-kbp EcoRI insert hybridized most strongly with the wound-induced cDNA probe and was isolated and characterized with restriction enzymes. A 2.6-kbp Taq I fragment was subjected to further restriction analysis and sequencing. FIG. 5 shows a restriction map of a 2.6-kbp fragment (pRT8) containing the inhibitor IIK gene, obtained from an 8-kbp insert from a potato genomic library in phage. The sequencing strategy for the structural gene and its flanking regions is shown below (i.e., arrows FIG. 5). Subclones were prepared in M13 vectors for sequencing, and arrows in FIG. 5 indicate the direction and the extent of the sequencing; and the following abbreviations are used in FIG. 5: namely, E, EcoRI; P, Pst I; B, BamHI; Hd, HindIII; A, Acc I; T, Taq I; R, Rsa I; S, Sau3A; Bc, Bcl I; Sc, Sca I; M, Msp I; Sp, Sph I; H, Hae III.

DNA Sequence Determination

To determine the nucleotide sequence of the gene and its 5' flanking regulatory sequences selected restriction fragments were obtained from a 2.6-kbp Taq I insert and cloned into various sites within M13 bacteriophage. Conditions for cloning, transformation, propagation of M13, isolation of both replicative form and single-stranded DNA, and dideoxy sequencing were by published procedures (Messing, J. et al., *Nucl. Acids Res.* 9:309–311, 1981; and, Vieira, J., et al. *Gene* 19:259–268, 1982).

Analyses of restriction fragments were carried out according to the method of Southern (Southern, E. *J. Mol. Biol.* 98:503–517, 1975). After restriction endonuclease digestion, DNA samples were separated on agarose gels, stained with ethidium bromide, denatured, neutralized, and transferred to GeneScreen membranes. Prehybridization solution contains 10% dextran sulfate, 50% deionized formamide, 1% NaDodSO$_4$, and 1 M NaCl. Hybridization was conducted in this same solution for 16 hr. following addition of boiled nick-translated inhibitor II cDNA (Graham, J. et al., supra.) and 100 μl of salmon sperm carrier DNA (10 mg/ml). The membranes were twice washed in 2xSSC at room temperature, then in 2xSSC/1% NaDodSO$_4$ for 30 min at 55° C. Autoradiography was performed for various times using a calcium tungstate intensifier screen. The nucleotide sequence of the potato inhibitor IIK gene and its coded protein is shown in FIG. 6 (Thornburg et al., supra.). The gene is similar to an inhibitor II gene isolated from the diploid potato line HH80 12017 (Keil, M. et al., *Nucleic Acids Res.* 14:5641–5650, 1986).

In the 5' region of the gene, the putative regulatory sequence TATAA is located 72 bp upstream from the initiation codon and 24 bp upstream from the transcription start, assumed by comparison with tomato inhibitor II cap site (Lee, J. et al., supra.) determined by primer extension experiments, at nucleotide 258 (heavy arrow, FIG. 6). FIG. 6 depicts the nucleotide sequence of a 1.24-kbp fragment of the inhibitor IIK gene and flanking sequences. The TATA box and polyadenylation signal AATAAG are underlined. Large arrow indicates the site of transcription initiation; the small arrow indicates the site of polyadenylylation in the homologous tomato inhibitor II cDNA sequences. The numbering of the amino acids begins at the NH$_2$ terminus of the transit sequence. The nascent protein is assumed to be processed during or after synthesis between amino acid residues 30 and 31 to produce the mature inhibitor.

Vector Constructions

The isolation and characterization of the proteinase inhibitor IIK gene from potatoes provided the opportunity to fuse the potential regulatory regions of this apparently wound-inducible gene to the open reading frame of the CAT gene to test the capabilities of the promoter and terminator to express CAT under wound-inducible control. An SCA I site in the inhibitor II gene (FIG. 5), 18 bases upstream from the translation initiation codon and 30 bases downstream from the putative transcription start site, was used to obtain a 1000-bp fragment of the 5' flanking regions of the gene for the vector construct. An Rsa I site 11 bp upstream from the termination codon of the inhibitor IIK gene provided a 3' fragment of ≈1000 bp that could also be used for the construction of the fused gene. The resulting construction, called pRT45 (Thornburg et al., supra.), eliminated almost all of the open reading frame of inhibitor IIK gene from potential translation, including the signal or transit sequence and the 117-bp intervening sequence. The essential components of the inhibitor IIK-CAT fused gene and its position in the transformation vector pRT45 are shown in FIG. 7.

The strategy for the construction was as follows: the 2.6-kbp Taq I fragment of a plasmid pRT8 (FIG. 5), containing the entire inhibitor IIK gene with the aforementioned 3' and 5' sequences, was purified from low melting agarose, then digested with Msp I, and the 1.35-kbp Taq I/Msp I fragment containing the 5' end of Inhibitor IIK was recovered and ligated into the Acc I site of pUC13. The insert was removed with Pst I (in the multilinker) and Sca I and ligated into a Pst I/HindII site of pUC13 to give plasmid pRT24. Sequencing of both ends verified that this clone contained the 5' end of the inhibitor IIK gene terminating 18 bp upstream from the ATG start codon. A 782-bp BglII/BamHI fragment, containing the entire coding region of the CAT gene, was isolated from pGA425 (Maniatis et al., supra.) and inserted into the unique BamHI site in the plasmid pRT24 at the downstream terminus of the inhibitor IIK promoter. A 1000-bp Rsa I fragment containing the 3' flanking region of the inhibitor IIK gene and 11 bp of the open reading frame with a TAA stop signal was inserted at the 3' end of the CAT gene to form pRT41. pRT41 was cloned into the HindIII site of pGA482 (An, G., Plant Physiol. 81:86–91, 1986), a binary Ti plasmid vector, to produce pRT45 to deliver the chimeric gene to plants.

The sequence of the chimeric gene at the 5' fusion (data not shown) demonstrated that the inhibitor IIK open reading frame plus 18 bp of the 5' untranslated region had been replaced with the CAT coding region and 42 bp of its own 5' untranslated region. This construction brought the translation initiation codon of the CAT gene to a position 80 bp downstream from the transcription initiation site as compared to 47 bp in the intact inhibitor IIK gene. The presence of the termination region of the inhibitor II gene in pRT41 was shown by Southern hybridization.

A second construction was identical to the pRT45 except that the 3' region of the inhibitor II gene in the construct was replaced with the terminator sequence of the 6b gene of pTiA6. In this construct, the plasmid pRT24 containing the 5' region of inhibitor II was inserted in pGA492 (An, G., supra.), which is a binary transformation vector containing the open reading coding region of CAT with the 6b terminator from the Ti plasmid. This vector has a polylinker site at the 5' terminus of the CAT coding region for cloning in selected promoter sequences. The 1000-bp inhibitor II 5' region was cloned into a Bgl II site of pGA492 to provide the identical fusion between the inhibitor II promoter and the CAT gene as found in pRT45. Therefore, the only difference in gene fusions between pRT45 and pRT50 was in the terminator region.

The two constructs pRT45 and pRT50 (FIG. 7) provided opportunity to directly compare the effects of the two terminators on the levels of expression of CAT regulated by the inhibitor IIK 5' region. FIG. 7 (Upper) depicts the constructs in the binary Ti vector containing 1000 bp of inhibitor IIK (INH II) 5' region beginning 18 bp upstream from the translation initiation codon and 1000 bp of the inhibitor IIK 3' beginning 11 bp upstream from the translation termination codon, fused with the open reading frame of the CAT gene (pRT45), and a similar construct containing the 5' region of the inhibitor IIK gene and the CAT open reading frame but with the 6b terminator of the Ti plasmid A6 in place of the inhibitor IIK terminator (pRK50). (Lower) A circular map pRT45. Hatched regions are from the inhibitor IIK gene and solid region is from pUC13 and the following abbreviations are used in FIG. 7; namely, $B_L$, T-DNA left border; $B_R$, T-DNA right border; nos-npt, a chimeric nos-npt fusion for a plant selectable marker; bla, β-lactamase gene; $Tc^R$, tetracycline resistance; $T_{INH\ II}$, inhibitor IIK terminator; $P_{INH\ II}$, inhibitor IIK promoter.

Transformation of Tobacco Tissues

To construct transgenic plants in which the foreign CAT gene operably-linked to Inhibitor II regulatory region could be tested, plasmids constructed in *E. coli* were transferred into *Agrobacterium tumefaciens* PC2760 containing the helper Ti plasmid AL4404 (Hoekema, A. et al., *Nature* 303:179–181, 1983) by the triparental mating method (Ditta, G. et al., *Proc. Natl. Acad. Sci. USA* 77:7347–7351, 1980). The structure of the transferred plasmids was analyzed after mating back to *E. coli*. Agrobacterium cells carrying both the helper Ti plasmid and the binary vector containing the inhibitor IIK-CAT fusion were cocultered for 2 days with leaf slices from sterile tobacco plants (An, G. et al., *Plant Physiol.* 81:301–305, 1986). The bacterial cells were washed away and transformed tobacco calli were selected on a Murashige-Skoog agar medium containing 3% sucrose, kanamycin (200 mg/liter), cefotaxime (250 mg/liter), and an appropriate amount of phytohormone (naphthalene acetic acid at 2 mg/liter and benzyladenine at 0.5 mg/liter for callus induction; benzyladenine at 0.5 mg/liter for shoot induction). The cocultivated plant cells were incubated at 28° C. under light (3000 lux) for 12 hr/day. Transformed tobacco tissues were visualized within 3–4 weeks after cocultivation. The tissues were transferred to another medium containing exactly the same ingredients and were further incubated as described above. Plants were regenerated on Murashige-Skoog agar medium containing the same concentration of sucrose and antibiotics but lacking the phytohormones. Regenerated plants were transferred to pots and grown in a greenhouse under natural light supplemented with artificial light.

Assays for Inductibility of the CAT Gene in Transgenic Plants

Figure 8A:
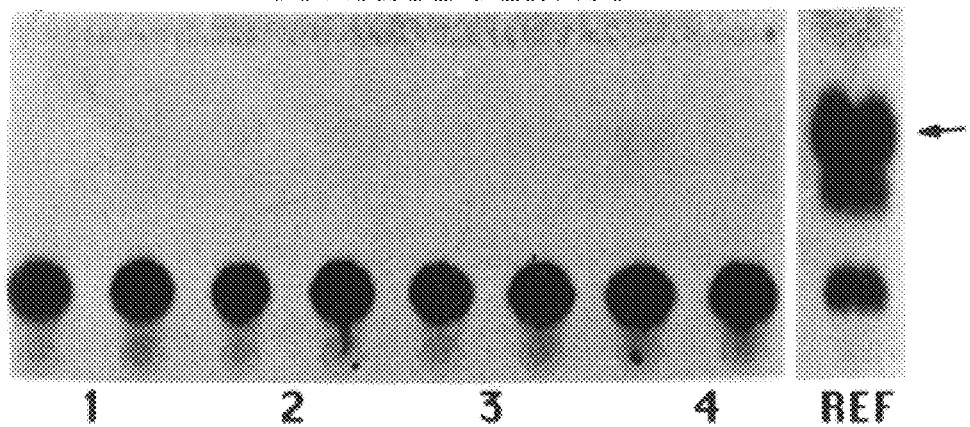
FIG. 8 depicts the results of experiments in which methyl jasmonate was used to induce the expression of a foreign gene in a transgenic tobacco plant engineered with the CAT gene ligated to wound-inducible 5' regulatory nucleotide sequences of a defense protein gene.
Figure 8B:
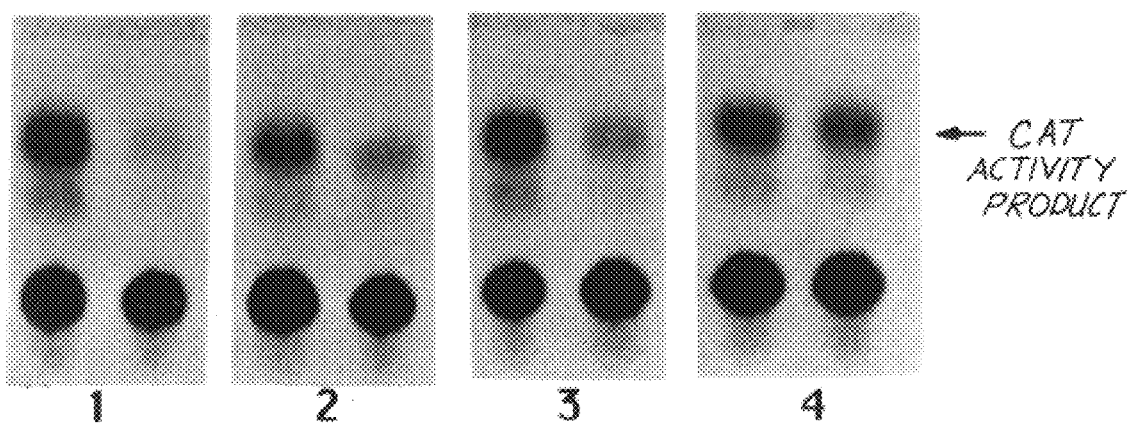

Transformed tobacco plants (20–30 cm tall) were used to assay for the methyl jasmonate-induced expression of CAT activity (Gorman, C. M. et al., *Mol. Cell. Biol.* 2:1044–1051, 1982). Each plant was placed in a sealed 1250 ml jar with a cotton swab containing either 1 ml of 10% (v/v) methyl jasmonate in ethanol or 1 μl ethanol as a control. After incubation for 20 hr. at 28° C. in constant light (300 $\mu Em^{-2}sec^{-1}$) two leaves from each plant were assayed for CAT activity using 100 μg leaf protein and an assay duration of 60 min. at 37° C. Extracts from tobacco leaves were prepared by grinding the leaves with a small mortar and pestle and expressing the juice from the debris by pressing with the pestle. The juice was centrifuged for 2 min at 10,000×g, and the clear supernatant was recovered for protein analysis by the method of Bradford. (Bradford, M., *Anal. Biochem.* 72:248–254, 1976). A quantity from each extract containing 100 μg of protein was assayed for CAT activity as described, using an assay duration of 60 min at 37° C. chloramphenicol as substrate (Gorman, C. M., et al., supra.). The results presented in FIG. 8 show CAT activity in duplicate samples (i.e., two leaves) from each of four (i.e., 1, 2, 3, 4) control or methyl jasmonate transgenic plants. Methyl jasmonate-induced expression of the foreign CAT gene coupled to the inhibitor II 5' flanking regulatory sequence in all four plants; no CAT activity was observed in the controls. These results show that methyl jasmonate induced expression of a foreign gene operably-linked to a defense protein 5' regulatory region (e.g., the inhibitor IIK gene presumptive 5' promoter region).

While the invention has been described in connection with representative embodiments and examples, various modifications and equivalents will be apparent to those skilled in the art from the foregoing specification. It is intended that such modifications and equivalents be within the scope of the appended claims, except insofar as precluded by the prior art.

What is claimed is:

1. A method of inducing the production of a protein in a plant comprising:

a) introducing into the plant a nucleotide sequence encoding the protein operably linked to a wound inducible 5' regulatory nucleotide sequence from a plant serine proteinase inhibitor gene, under conditions permitting expression of the protein encoding nucleotide sequence in the plant; and then b) contacting the plant with an amount effective to induce production of the protein by the plant of an inducing agent of formula I, II or III:

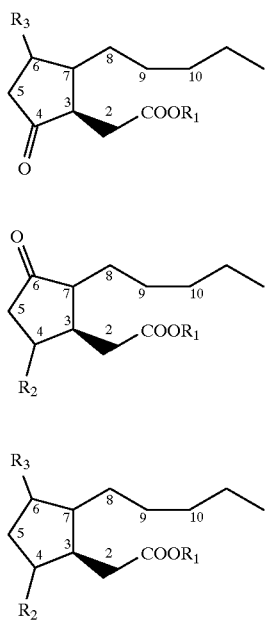

wherein $R_1$ is H, lower alkyl having from 1 to 6 carbon atoms or a carrier ligand; $R_2$ and $R_3$ are independently selected from —H, —OH, or lower alkyl having from 1 to 6 carbon atoms; and the agent is optionally single or double bonded at the $C_2$:$C_3$, $C_3$:$C_4$, $C_3$:$C_7$, $C_4$:$C_5$, $C_5$:$C_6$, $C_6$:$C_7$, or $C_9$:$C_{10}$ bonds, provided that $C_3$:$C_4$ and $C_4$:$C_5$ can not be double bonded in formula I and that $R_5$:$R_6$ and $R_6$:$R_7$ can not be double bonded in formula II.

2. The method of claim 1, wherein the protein encoding nucleotide sequence encodes a predator defense protein.

3. The method of claim 1, wherein the protein encoding nucleotide sequence is a foreign gene.

4. The method of claim 1, wherein the inducing agent is selected from the group consisting of jasmonic acid, 7-isojasmonic acid, 9,10-dihydrojasmonic acid, 2,3-didehydrojasmonic acid, 3,4-didehydrojasmonic acid, 3,7-didehydrojasmonic acid, 4,5-didehydrojasmonic acid, 5,6-didehydrojasmonic acid, 6,7-didehydrojasmonic acid, 7,8-didehydrojasmonic acid, and the lower alkyl esters, the carrier ligand conjugates and the stereoisomers thereof.

5. The method of claim 4, wherein the inducing agent is jasmonic acid or methyl jasmonate.

6. The method of claim 1, wherein the plant is contacted with the inducing agent by treating the plant with a solution of the agent.

7. The method of claim 1, wherein the plant is contacted with the inducing agent by placing a volatile source of the agent sufficiently close to the plant to effect induction at dispersal concentration.

8. The method of claim 1, wherein the protein are selected from the group consisting of proteinase inhibitors, thionins, chitinases, β-glucanases, casbene synthase, enzymes in the phenylpropenoid pathway, enzymes in the terpenoid pathway, and enzymes of alkaloid synthesis.

9. The method of claim 1, wherein the protein is a proteinase inhibitor.

10. The method of claim 1, wherein the wound inducible 5' regulatory nucleotide sequence from a plant serine proteinase inhibitor gene is a wound inducible 5' regulatory nucleotide sequence from a serine proteinase inhibitor gene encoding an inhibitor protein selected from the group consisting of the soybean trypsin inhibitor (Kunitz) family, the soybean proteinase inhibitor (Bowman-Birk) family, the potato I family, the potato II (inhibitor II) family, the barley trypsin inhibitor family, and the squash inhibitor family.

* * * * *